United States Patent [19]

Rim et al.

[11] 4,028,437

[45] June 7, 1977

[54] DODECAHALO-9,10-OXADECAHYDRO-1,4:5,8-DIMETHANOANTHRACENE FLAME RETARDANTS FOR POLYMERS

[75] Inventors: Yong S. Rim, Waterbury; Walter Nudenberg, Newtown, both of Conn.

[73] Assignee: Uniroyal Inc., New York, N.Y.

[22] Filed: Jan. 28, 1976

[21] Appl. No.: 653,164

Related U.S. Application Data

[62] Division of Ser. No. 492,643, July 29, 1974, Pat. No. 3,976,664.

[52] U.S. Cl. .................. 260/880 R; 260/45.75 B; 260/45.8 A; 260/878 R
[51] Int. Cl.² ...................... C08K 5/59; C08K 5/15
[58] Field of Search ............... 260/45.75 B, 45.8 A, 260/878 R, 880 R

[56] References Cited

UNITED STATES PATENTS

| | | | |
|---|---|---|---|
| 2,655,513 | 10/1953 | Kleiman | 260/346.2 M |
| 2,705,235 | 3/1955 | Kleiman | 260/346.2 M |
| 2,733,248 | 1/1958 | Lidov | 260/45.8 A |
| 3,274,217 | 9/1966 | Dombro | 260/45.8 A |
| 3,632,544 | 1/1972 | Boyer | 260/346.2 M |
| 3,687,983 | 8/1972 | Dever et al. | 260/346.2 M |
| 3,991,011 | 11/1976 | Marciniak | 260/45.8 A |

*Primary Examiner*—V.P. Hoke
*Attorney, Agent, or Firm*—Bert J. Lewen

[57] ABSTRACT

There are disclosed novel, dodecahalo-9,10-oxadecahydro-1,4:5,8-dimethanoanthracenes which are useful as flame retardant additives for acrylonitrilebutadiene-styrene (ABS) gum plastics and other polymeric materials, and a method for preparing these novel anthracenes.

21 Claims, No Drawings

DODECAHALO-9,10-OXADECAHYDRO-1,4:5,8-DIMETHANOANTHRACENE FLAME RETARDANTS FOR POLYMERS

This is a division, of application Ser. No. 492,643, filed Jul. 29, 1974 now U.S. Pat. No. 3,976,664.

This invention relates to novel dodecahalo-9,10-oxadecahydro-1,4:5,8-dimethanoanthracenes, a method for their preparation, and their use as flame retardant additives for acrylonitrile-butadiene-styrene (ABS) gum plastics and other polymeric materials.

BACKGROUND OF THE INVENTION

The increased use of polymeric materials, particularly in the building industry, has resulted in increased interest in rendering these materials fire retardant or flameproof. Presently, most commercially available plastics do not possess satisfactory fire retardancy and this inadequacy represents one of the major obstacles to the use of these materials.

The most widely accepted fire retardant chemicals now in use with polymeric materials are antimony trioxide and organohalogen compounds. Of the organohalogen compounds, the best known are chlorendic anhydride (1,4,5,6,7,7-hexachlorobicyclo[2.2.1]-hept-5-ene-2,3-dicarboxylic anhydride); tetrabromo- or tetrachlorophthalic acid; 1,4'-isopropylidenebis(2,6-dichlorophenol) [tetrachlorobisphenol A] or the corresponding bromine-containing compound; Cloran (trademark), i.e., 2,3-dicarboxyl-5,8-endomethylene-5,6,7,8,9,9-hexachloro-1,2,3,4,4a,5,8,8a-octahydronaphthalene anhydride; chlorinated paraffins; and dechlorane (dihexachlorocyclopentadiene).

These organohalogen compounds have only limited utility in polymer compositions due to a number of disadvantages. For example, when such halogen compounds are incorporated into a polymer, various physical properties of the polymer are modified, e.g., change in melt viscosity, which requires higher processing temperatures, decrease in light stability, decrease in thermal stability, increase in density, adverse effects on heat distortion temperature, etc.

Some of these disadvantages have been overcome by the use of halogen-containing polymers as the flame retardant additive. Typical of such polymers are 2-chloropolybutadiene, polyvinylchloride, chlorinated polyethylene and chlorosulfonated polyethylene. However, serious disadvantages are also associated with the use of such polymers. Among these disadvantages are: (1) large amounts of halogen-containing polymers are required in order to obtain satisfactory fire retardancy due to the relatively low halogen content thereof; (2) the halogen-containing polymers have low thermal stabilities; and (3) the blending of the halogen-containing polymer with the polymer to be rendered flame retardant usually requires expensive processing techniques.

Some prior art patents are noteworthy for their disclosures of organohalogen compounds proposed for use as flame retardants for polymeric compositions. For example, U.S. Pat. No. 3,403,036 describes a flame retardant having the general formula:

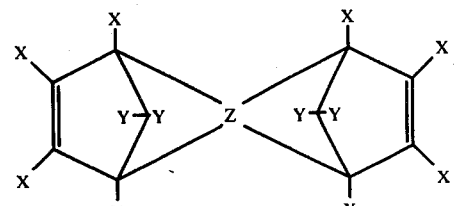

wherein X is selected from the group consisting of bromine, chlorine and fluorine; Y is selected from the group consisting of bromine, chlorine, fluorine, alkyl and alkoxy; and Z is a tetravalent cyclic hydrocarbon radical containing at least five carbon atoms. In each case specified in this patent, each reactant forming the Z radical is characterized as being a cyclic hydrocarbon having two centers of unsaturation. In contrast, the novel compounds of this invention have an oxo bridge between the two centers.

Belgian Patent No. 754,358 discloses the use of furan adducts as flame retardants for polymeric compositions wherein the furan adducts have the general formula:

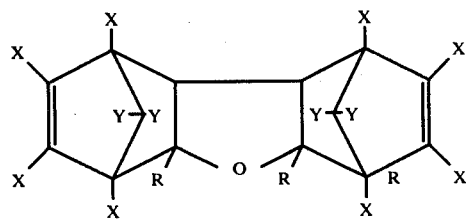

wherein x is halogen, such as fluorine, chlorine or bromine; Y is fluorine, chlorine or bromine or an alkyl, alkoxy, haloalkyl or haloalkoxy, each having 1–10 carbon atoms; and R is hydrogen or an alkyl having 1–6 carbon atoms. In this patent, the furan is used as a dienophile, whereas in the present invention, the furan is used first as a diene and then as a dienophile.

These prior art compounds have been discussed in some detail in order to emphasize the structural differences between these prior art compounds and those of this invention as will become more apparent from the ensuing description of the invention.

The Invention

The novel dodecahalo-9,10-oxadecahydro-1,4:5,8-dimethanoanthracenes of the invention have the general formula:

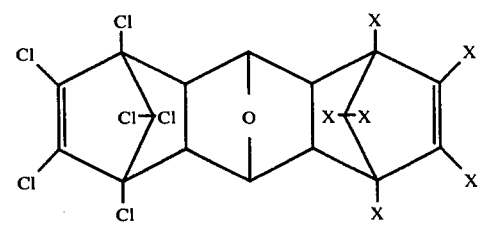

wherein X is chlorine or bromine.

Of the compounds falling within this general formula, the preferred compounds are: 1,2,3,4,5,6,7,8,11,11,12,12-dodecachloro-1,4,4a,10,10a,5,8,8a,9,9a-decahydro-1,4:5,8-dimethano-9,10-oxaanthracene, found to be useful as a flame retardant for ABS gum plastics and hereinafter identified as "DDDEA"; and the compound 1,2,3,4,11,11-hexabromo-5,6,7,8,12,12-hexachloro-1,4,4a,10,10a,5,8-,8a,9,9a-decahydro-1,4:5,8-dimethano-9,10-oxaanthracene, hereinafter identified as "HHDDEA."

The present invention also provides a method for preparing these novel compounds. For example, DDDEA can generally be obtained by adding one mole of furan to an excess of hot (110°-140° C.) hexachloronorbornadiene and then adding one mole of hexachlorocyclopentadiene. Within thirty minutes, a white precipitate of DDDEA forms while the reaction mixture is still hot. Reasonably pure DDDEA is obtained after cooling the reaction mixture to room temperature and filtering.

The fire retardant additive, DDDEA, can readily be incorporated into polymeric materials by a variety of methods depending on the nature of the polymeric material. For example, for those polymers which are adaptable to milling procedures such as ABS gum plastics, polyurethanes, ethylene propylene diene (EPDM)-polypropylene blends and the like, the fire retardant may simply by physically blended with the preformed polymer. With other types of polymers such as those which require compounding, e.g., an uncured elastomer, or those which cannot readily be physically blended with other materials after formation of the polymer, the fire retardant may be added to the compounding mixture or to the polymerization mixture. Improved fire retardance can be provided by incorporating antimony oxide into the fire retardant composition. The fire retardant compositions obtained in this manner do not affect the desirable physical properties to be retained in ABS gum plastics or other polymeric materials, particularly impact resistance, hardness, heat distortion temperature and processing characteristics.

Regardless of the methods used to manufacture the polymeric materials, the fire retardants of the invention are incorporated therein in amounts of about 5–35 parts by weight of fire retardant per 100 parts polymer, preferably 15–30 parts by weight of fire retardant per 100 parts polymer. When antimony oxide is included, it can be present in amounts of about 3–15 parts by weight per 100 parts polymer, preferably 6 to 12 parts by weight per 100 parts polymer.

The novel compounds of the invention, their preparation, and utility as flame retardants will become more clear from the ensuing examples which are set forth to illustrate the invention and are not intended to be, nor should they be construed as being, limitative of the invention. In the following examples, hexachloronorbornadiene and hexachlorocyclopentadiene are commercially available starting materials. Hexabromocyclopentadiene can be prepared according to the method disclosed in U.S. Pat. No. 3,506,726.

EXAMPLE 1

Preparation of
1,2,3,4,5,6,7,8,11,11,12,12-dodecachloro-1,4,4a,10,-10a,5,8,8a,9,9a-decahydro-1,4:5,8-dimethano-9,10-oxaanthracene (DDDEA)

A. Two step synthesis:

Hexachloronorbornadiene (150 g., 0.5 mole) and 50 ml. toluene were heated under nitrogen at approximately 120° C. and furan (27.2 g., 0.4 mole) was added under the surface of the solution at such a rate so as to maintain the reaction temperature above 100° C. This took approximately 21 hours. The reaction mixture was then cooled to room temperature. A solid formed and was filtered off. The crude, dried solid weighed 102.8 g. (about 70% yield). The product was a Diels-Alder adduct (furan acted as a diene) 1,2,3,4,10,10-hexachloro-1,4,4a,5,8,8a-hexahydro-5,8-oxa-1,4-methanonaphthalene (HHEM).

HHEM (36 g., 0.1 mole), hexachlorocyclopentadiene (30 g., 0.11 mole) and 20 ml. of toluene were mixed and gently refluxed for two hours. The reaction mixture solidified on cooling to room temperature. The solid was washed with Skelly B solvent twice, dried, and yielded a white powdery material which did not melt up to 300° C. The total yield of DDDEA was 58.8 g. (about 94% based on HHEM). The NMR spectrum and elemental analysis were consistent with the proposed structure. Anal. calc'd. for $C_{16}H_6Cl_{12}O(\%)$: C, 30.03; H, 0.97; Cl, 66.52; Found (%): C, 29.81; H, 1.14; Cl, 65.75

B. One step synthesis:

Hexachloronorbornadiene (300 g., 1 mole) and 100 ml. of xylene were heated at 140° C. and then 68 g. of furan (1 mole) was added under the surface of the solution at such a rate so as to maintain the reaction temperature above 100° C. This took approximately 24 hours. The reaction mixture was then cooled to 60° C. and 273 g. of hexachlorocyclopentadiene (1 mole) was added at once and the reaction mixture was heated at 140° C. for two hours. After cooling to room temperature, the white solid which formed was filtered on a Buchner funnel and washed twice with 200 ml. of Skelly B solvent. The white powdery DDDEA obtained did not melt up to 300° C. and weighed 458.5 g. (about a 70.1% yield based on furan).

The NMR spectrum and elemental analysis were consistent with the proposed structure.

Anal. calc'd (%): C, 30.03; H, 0.97; Cl, 66.52 Found (%): C, 29.93; H, 1.05; Cl, 65.97

In either the two-step synthesis (A) or one-step synthesis (B) described above, the hexachlorocyclopentadiene can be replaced with hexabromocyclopentadiene to obtain HHDDEA as illustrated below.

EXAMPLE 2

Preparation of
1,2,3,4,11,11-hexabromo-5,6,7,8,12,12-hexachloro-1,4,4a,10,10a,5,8,8a,9,9a-decahydro-1,4:5,8-dimethano-9,10-oxaanthracene (HHDDEA)

1,2,3,4,10,10-Hexachloro-1,4,4a,5,8,8a-hexahydro-5,8-oxa-1,4-methanonaphthalene (HHEM) (36 g., 0.1 mole) and 54.0 g. of hexabromocyclopentadiene was dissolved in 300 ml. of chlorobenzene and refluxed for 6 hours. After about 30 minutes heating at the reflux temperature, a white solid began to form. The reaction mixture was cooled to room temperature and the white solid which formed was filtered off. This solid was recrystallized from benzene and white needle like crystals were obtained which did not melt up to 300° C. Infrared analysis showed sharp norbornene at 1600 cm$^{-1}$. The elemental analysis was as follows:

Calc'd. (%): Br, 52.90; Cl, 23.47 Found (%): Br, 50.45; Cl, 22.80

EXAMPLE 3

This Example illustrates the use of the compounds of the invention when incorporated in an ABS gum plastic. Suitable ABS gum plastics are set forth in U.S. Pat. No. 3,686,362, col. 1, line 50 to col. 3, line 21 and in U.S. Pat. No. 3,649,712, col. 2, line 37 to col. 4, line 37, which citations are hereby incorporated herein by reference.

Varying amounts of fire retardant additives were milled into Kralastic MV ABS resin and compression molded. Kralastic MV is a graft polymer containing, by weight, 22% acrylonitrile, 23% butadiene and 55% styrene, and is characterized by a sp. gr. (ASTM D792-60T) of 1.02; izod, notched (ASTM D256-56) of 6.5 ft.-lbs./inch notch; tensile strength (ASTM D638-61T) of 5,000; flexural strength (ASTM D790-63) of 7,500 psi; Rockwell Hardness (ASTM D785-62) of 96; and a heat deflection temperature (ASTM D648-56) of 195° F. Test strips of the polymer were evaluated for fire retardance using ASTM D-635, hereinafter referred to as "burn rate," and ASTM D-2863, hereinafter referred to as "Oxygen Index." For the burn rate, the test strips were ⅛ inch × ½ inch × 5 inches and for the Oxygen Index, the test strips were ⅛ inch × ¼ inch × 2½ inches.

As defined in ASTM D-2863, Oxygen Index is the minimum concentration of oxygen, expressed as percent by volume, in a slowly rising oxygen concentration in a mixture of nitrogen and oxygen, that will just support the combustion of a material burning under equilibrium conditions of candle-like burning. Higher Oxygen Index indicates decreased relative flammability. Since the method provides a continuous numerical scale for the assignment of relative flammability ratings, it is especially appropriate for illustrating differences in the degree of flame retardation provided by additives and additive combinations. The "ΔOI" values where shown represent the increase in Oxygen Index provided by the additive or additive combination over that of the base polymer.

Three or more test specimens were employed in the burn rate test. Compositions which failed to burn to the 4-inch mark are designated as "SE" (self-extinguishing), while compositions which failed to burn to the 1-inch mark are designated as "NB" (non-burning).

The results of the tests are shown below in Table I.

TABLE I

Evaluation of Fire Retardant Additives in ABS Gum Plastic

| Additive(s) | PPH | Burn Rate (in./min.) | Oxygen Index | ΔOI |
|---|---|---|---|---|
| None | — | 1.61 | 18.5 | — |
| DDDEA | 10 | 1.30 | 19.4 | + 0.9 |
| DDDEA | 15 | 1.30 | 21.7 | + 3.2 |
| DDDEA, $Sb_2O_3$ | 15, 4 | S.E. | 25.2 | + 6.7 |
| HHDDEA | 15 | 0.70 | 22.0 | + 3.5 |
| HHDDEA, $Sb_2O_3$ | 15, 4 | N.B. | 25.7 | + 7.2 |
| Cloran | 11 | 1.33 | 19.0 | + 0.5 |
| Cloran | 25 | 1.40 | 21.4 | + 2.9 |
| Cloran, $Sb_2O_3$ | 15, 4 | 1.71 | 22.1 | + 3.6 |
| Cloran, $Sb_2O_3$ | 15, 6 | 1.51 | 23.4 | + 4.9 |
| Cloran, $Sb_2O_3$ | 20, 6 | N.B. | 24.7 | + 6.2 |

As shown in Table I, DDDEA at the 15 pph level with 4 pph of antimony oxide, gave a self-extinguishing composition and an Oxygen Index of 25.2 while the Oxygen Index for the corresponding Cloran-antimony oxide combination is 22.1. HHDDEA at 15 pph level gives an Oxygen Index of 22.0, while at the 15 pph level with 4 pph of antimony oxide it gives a non-burning composition and an Oxygen Index of 25.7. These results show that DDDEA and HHDDEA are superior to Cloran by these tests and that antimony oxide has a synergistic effect when used with the compounds of the invention.

EXAMPLE 4

This Example illustrates the results obtained when plastics containing the compounds of the invention are subjected to the burn rate test.

Varying amounts of fire retardant additives were milled into the same ABS plastic as was used in Example 3 above and compression molded. Three or more test specimens, 6 inches × ½ inches × 1/16 inches, were tested by the Underwriters Laboratories, Subject 94 test, a vertical burning test, for rating materials, "S.E.-O," "S.E.-I," or "S.E.-II," these ratings being defined following Table II. The results are shown in Table II below. In Table II, the compound designated A* is a representative compound prepared pursuant to U.S. Pat. No. 3,403,036, which was incorporated in the ABS plastic and subjected to the same tests as were the other compounds shown in this table.

*1,4,7,10-dimethanocycloocta-1,2,3,4,7,8,9,10,13,13,14,14-dodecachloro-1,4,4a,5,6,6a,7,10,10a,11,12,12a-dodecahydro[1,2,5,6]-dibenzene.

TABLE II

| Additives | pph in ABS | UL 94 (V, 1/16″) |
|---|---|---|
| DDDEA, $Sb_2O_3$ | 22, 8 | S.E.-II |
| DDDEA, $Sb_2O_3$ | 24, 6 | F |
| DDDEA, $Sb_2O_3$ | 26, 11 | S.E.-O |
| DDDEA, $Sb_2O_3$ | 26, 10 | S.E.-O |
| HHDDEA, $Sb_2O_3$ | 20, 8 | F. |
| HHDDEA, $Sb_2O_3$ | 20, 10 | S.E.-O |
| HHDDEA, $Sb_2O_3$ | 17, 10 | S.E.-I |
| Cloran, $Sb_2O_3$ | 24, 10 | F |
| Cloran, $Sb_2O_3$ | 30, 11 | S.E.-O |
| A, $Sb_2O_3$ | 30, 11 | S.E.-O |

| Rating | Meaning |
|---|---|
| S.E.-O | Extinguishing within 5 seconds and non-dripping. |
| S.E.-I | Extinguishing within 30 seconds and non-dripping. |
| S.E.-II | Extinguishing within 30 seconds but ignites the cotton. |
| F | Sample consumed completely by burning. |

As can be seen from Table II, in order to render ABS self-extinguishing (S.E.-O rating by UL-94 (V) test), 26 pph of DDDEA are required and 10 pph of antimony oxide, or 20 pph or HHDDEA and 10 pph of antimony oxide. By comparison, 30 pph of Cloran or compound A and 11 pph of antimony oxide are necessary to achieve the same S.E.-O rating.

EXAMPLE 5

Varying amounts of fire retardant additives were milled into Roylar E-85 polyurethane elastoplastic (polytetramethylene ether glycol based) and compression molded. Roylar E-85 is characterized by a specific gravity of 1.12; a durometer hardness (ASTM D-2240) of 85A; and a solenoid brittle point (ASTM D-746) of less than −90° F. Fire retardant tests were run according to the ASTM D-635 test and the ASTM D-2863 Oxygen Index method described hereinabove. The results obtained are shown in Table III below. The properties of the polyurethane used were as follows:

| Properties of Polyurethane | |
|---|---|
| Hardness (ASTM D-2240-68) | 91A |
| Modulus: psi 100% (ASTM D-412-68) | 1140 |
| psi 300% | 3090 |
| Tensile strength, psi (ASTM D-412-68) | 8050 |
| Elongation, % (ASTM D-412-68) | 500 |
| Specific Gravity | 1.12 |

-continued

Properties of Polyurethane (ASTM D-792-66)

TABLE III

| Additive | pph in Polyurethane | Dripping* | D-635 Burn Rate (in./min.) | D-2863 Oxygen Index | ΔO.I. |
|---|---|---|---|---|---|
| — | — | heavy | 1.03 | 21.0 | — |
| DDDEA | 10 | light | 0.61 | 22.0 | + 1.0 |
| DDDEA | 20 | none | 0.71 | 22.2 | + 1.2 |
| DDDEA | 25 | none | S.E. | 23.3 | + 2.3 |
| HHDDEA | 20 | none | S.E. | 24.0 | + 3.0 |
| Cloran | 10 | moderate | 0.68 | 22.9 | + 1.9 |
| Cloran | 25 | light | S.E. | 22.5 | + 1.5 |

*Determined by visual observation.

One of the most difficult problems for the flame-proofing of polyurethane is the dripping of flaming particles during combustion. As shown in Table III, both DDDEA and HHDDEA at the 20 pph levels gave nondripping and self-extinguishing compositions by the D-635 test. By comparison, Cloran at the 25 pph level in polyurethane gave a self-extinguishing composition but still drips.

EXAMPLE 6

Varying amounts of fire retardant additives were milled into TPR* 2800 EPDM-polypropylene blend (75/25 by weight) and compression molded. Suitable blends of this type are set forth in U.S. Pat. No. 3,758,643, which patent is hereby incorporated herein by reference. TPR 2800 contains 36.5% ethylene, 60% propylene and 3.5% of a non-conjugated diene, and is characterized by a specific gravity of 0.88; Shore A hardness of 87; ultimate tensile strength of 1350 psi; and an ultimate elongation of 180%. Fire retardant tests were obtained according to the same ASTM D-635 and D-2863 methods described hereinabove and the results are listed in Table IV below. The properties of the blend employed were as follows, these properties being obtained in the same manner as in Example 5 above:

| Properties of EPDM-Polypropylene Blend (75/25 by Weight) | |
|---|---|
| Hardness | 87 |
| 100% Modulus, psi | 1200 |
| Tensile Strength, psi | 1200 |
| Elongation, % | 150 |
| Specific Gravity | 1.88 |

*Trademark

TABLE IV

| Additive | PPH | Dripping* | D-635 Burn rate (in./min.) | D-2863 Oxygen Index | ΔOI |
|---|---|---|---|---|---|
| — | — | heavy | 1.20 | 17.7 | — |
| DDDEA | 10 | heavy | 0.92 | 18.9 | + 1.2 |
| DDDEA | 20 | moderate | 0.87 | 19.6 | + 1.9 |
| DDDEA | 30 | light (⅓ SE)** | 0.77 | 20.6 | + 2.9 |
| HHDDEA | 20 | light | 0.50 | 21.3 | + 3.6 |
| Cloran | 10 | heavy | 0.88 | 19.3 | + 1.6 |
| Cloran | 20 | heavy | 0.80 | 20.3 | + 2.6 |
| Cloran | 30 | heavy | 0.90 | 20.6 | + 2.9 |

*Determined by visual observation.
**Denotes one sample out of three was self-extinguishing.

In the fire retardant technology of polypropylene or EPDM, dripping of flaming particles during combustion is a very serious and difficult problem. As shown in Table IV, DDDEA at the 30 pph level and HHDDEA at the 20 pph level gave almost non-dripping, slow burning compositions, while cloran at the same level gives slow burning but drips heavily during the burning test.

EXAMPLE 7

Various flame-retardant additives were incorporated into the ABS gum plastic as described in Example 3 above and the physical properties of the resultant product were determined to illustrate that the additives of the invention do not deleteriously affect the physical properties of the plastic materials with which they are used. The results of these determinations are set forth in Table V below wherein heat distortion was determined by ASTM D648-72, impact strength (notched Izod), was determined by ASTM D256-72a, and Rockwell hardness (R scale) was determined by ASTM D785-65 (1970).

TABLE V

| | Physical Properties of ABS Gum Plastic | | | |
|---|---|---|---|---|
| Additive | pph | Heat Distortion (° C.) | Impact Strength (ft. lbs.) | Rockwell Hardness |
| None | — | 88 | 4.7 | 94 |
| DDDEA | 10 | 88 | 1.30 | 93 |
| Cloran | 25 | 88 | 0.79 | 91 |
| DDDEA, $Sb_2O_3$ | 15, 4 | 85 | 0.99 | 89 |
| Cloran, $Sb_2O_3$ | 15, 4 | 85 | 0.79 | 89 |

As can be seen from the results shown in Table V above, both DDDEA and Cloran at the additive, $Sb_2O_3$ pph level of 15, 4 decrease impact strength with DDDEA showing better performance whereas the effect on heat distortion and hardness is the same for both additives with or without $Sb_2O_3$.

While the invention has been described with particularity and in some detail, it should be understood that various changes and modifications can be made therein, as will become apparent to those skilled in the art, without departing from the scope and spirit of the invention.

What is claimed is:
1. A flame retardant composition comprising an organic polymer selected from the group consisting of hydrocarbon polymers, nitrile-containing polymers, and polyurethane polymers; and an effective flame retardant amount of a compound having the formula

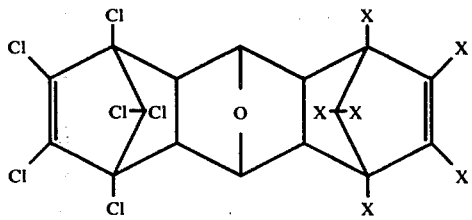

in which all of the X substituents are either chlorine or bromine.

2. A flame retardant composition comprising an organic polymer selected from the group consisting of hydrocarbon polymers, nitrile-containing polymers, and polyurethane polymers; and an effective flame retardant amount of the compound 1,2,3,4,5,6,7,8,11,11,12,12-dodecachloro-1,4,4a,10,-10a,5,8,8a,9,9a-decahydro-1,4:5,8-dimethano-9,10-oxaanthracene.

3. A flame retardant composition comprising an organic polymer selected from the group consisting of hydrocarbon polymers, nitrile-containing polymers, and polyurethane polymers; and an effective flame retardant amount of the compound 1,2,3,4,11,11,-hexabromo-5,6,7,8,12,12-hexachloro-1,4,4a,10,10a,5,8-,8a,9,9a-decahydro-1,4:5,8-dimethano-9,10-oxaanthracene.

4. The composition of claim 2 wherein the compound 1,2,3,4,5,6,7,8,11,11,12,12-dodecachloro-1,4,4a,10,-10a5,8,8a,9,9a-decahydro-1,4:5,8-dimethano-9,10oxaanthracene is present in an amount of about 5 to 35 parts by weight per 100 parts by weight of said organic polymer.

5. The composition of claim 2 wherein the compound 1,2,3,4,5,6,7,8,11,11,12,12-dodecachloro-1,4,4a,10,-10a,5,8,8a,9,9a-decahydro-1,4:5,8-dimethano-9,10-oxaanthracene is present in an amount of about 15 to 30 parts by weight per 100 parts by weight of said organic polymer.

6. The composition of claim 3 wherein the compound 1,2,3,4,11,11-hexabromo-5,6,7,8,12,12-hexachloro-1,4,4a,10,10a,5,8,8a,9,9a-decahydro-1,4:5,8-dimethano-9,10-oxaanthracene is present in an amount of about 5 to 35 parts by weight per 100 parts by weight of said organic polymer.

7. The composition of claim 3 wherein the compound 1,2,3,4,11,11-hexabromo-5,6,7,8,12,12-hexachloro-1,4,4a,10,10a,5,8,8a,9,9a-decahydro-1,4:5,8-dimethano-9,10-oxaanthracene is present in an amount of about 15 to 30 parts by weight per 100 parts by weight of said organic polymer.

8. The composition of claim 1 wherein said nitrile-containing polymer is a graft copolymer of acrylonitrile, butadiene and styrene.

9. The composition of claim 1 wherein said hydrocarbon polymer is a blend of (A) an ethylene, propylene and non-conjugated diene terpolymer rubber and (B) polypropylene, the weight ratio of A to B being about 75 to 25.

10. The composition of claim 1 wherein said polyurethane polymer is a polytetramethylene ether glycol polyurethane.

11. A flame retardant composition comprising a graft copolymer of acrylonitrile, butadiene and styrene, an effective flame retardant amount of a compound having the formula

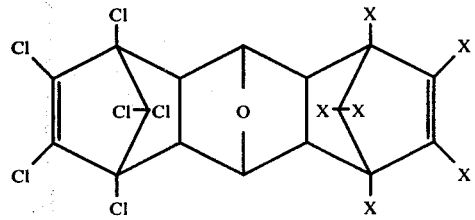

in which all of the X substituents are either chlorine or bromine and a compound of antimony.

12. The composition of claim 11 wherein the antimony compound is antimony oxide.

13. The composition of claim 12 wherein the compound having the formula

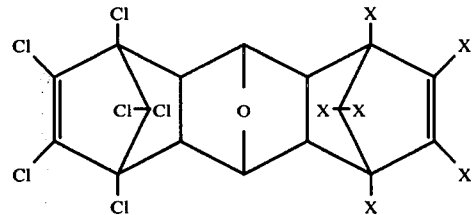

in which all of the X substituents are either chlorine or bromine is present in an amount of about 5 to 35 parts by weight per 100 parts by weight of said graft copolymer and said antimony oxide is present in an amount of about 3 to 15 parts by weight per 100 parts by weight of said graft copolymer.

14. A flame retardant composition comprising a polytetramethylene ether glycol polyurethane and an effective flame retardant amount of the compound 1,2,3,4,5,6,7,8,11,11,12,12-dodecachloro-1,4,4a,10,-10a,5,8,8a,8,8a-decahydro-1,4:5,8-dimethano-9,10-oxaanthracene.

15. The composition of claim 14 wherein the compound 1,2,3,4,5,6,7,8,11,11,12,12-dodecachloro-1,4,4a,10,10a,5,8,8a,9,9a-decahydro-1,4:5,8-dimethano-9,10-oxaanthracene is present in an amount of about 5 to 35 parts per 100 parts of said polyurethane.

16. A flame retardant composition comprising a polytetramethylene ether glycol polyurethane and an effective flame retardant amount of the compound 1,2,3,4,11,11-hexabromo-5,6,7,8,12,12-hexachloro-1,4,4a,10,10a,5,8,8a,9,9a-decahydro-1,4:5,8-dimethano-9,10-oxaanthracene.

17. The composition of claim 16 wherein the compound 1,2,3,4,11,11-hexabromo-5,6,7,8,12,12-hexachloro-1,4,4a,10,10a,5,8,8a,9,9a-decahydro-1,4:5,8-dimethano-9,10-oxaanthracene is present in an amount of about 5 to 35 parts per 100 parts of said polyurethane.

18. A flame retardant composition comprising a hydrocarbon polymer which is a 75:25 weight ratio blend of an ethylene, propylene, non-conjugated diene terpolymer rubber and polypropylene and an effective flame retardant amount of the compound 1,2,3,4,5,6,7,8,11,11,12,12-dodecachloro-1,4,4a,1,-10a,5,8,8a,9,9a-decahydro-1,4:5,8-dimethano-9,10-oxaanthracene.

19. The composition of claim 18 wherein the compound 1,2,3,4,5,6,7,8,11,11,12,12-dodecachloro-1,4,4a,10,10a,5,8,8a,9,9a-decahydro-1,4:5,8-dimethano-9,10-oxaanthracene is present in an amount of about 5 to 35 parts per 100 parts of said hydrocarbon polymer.

20. A flame retardant composition comprising a hydrocarbon polymer which is a 75:25 weight ratio blend of an ethylene, propylene, non-conjugated diene terpolymer rubber and polypropylene and an effective flame retardant amount of the compound 1,2,3,4,11,11-hexabromo-5,6,7,8,12,12-hexachloro-1,4,4a,10,10a,5,8,8a,9,9a-decahydro-1,4:5,8-dimethano-9,10-oxaanthracene.

21. The composition of claim 20 wherein the compound 1,2,3,4,11,11-hexabromo-5,6,7,8,12,12-hexachloro-1,4,4a,10,10a,5,8,8a,9,9a-decahydro-1,4:5,8-dimethano-9,10-oxaanthracene is present in an amount of about 5 to 35 parts per 100 parts of said hydrocarbon polymer.

* * * * *

UNITED STATES PATENT AND TRADEMARK OFFICE
CERTIFICATE OF CORRECTION

PATENT NO. : 4,028,437
DATED : June 7, 1977
INVENTOR(S) : YONG S. RIM and WALTER NUDENBERG It is certified that error appears in the above–identified patent and that said Letters Patent are hereby corrected as shown below:

Col. 9, Claim 3, line 32, "1,2,3,4,11,11,-hex-" should read --1,2,3,4,11,11-hex- --

Col. 9, Claim 4, line 38, note the following, "10a5," should read --10a,5,--; and "10ox-" should read --10-ox---

Col. 10, Claim 14, line 45, note the following "5,8,8a,8,8a" should read --5,8,8a,9,9a--

Col. 11, Claim 18, line 1, the following "4a,1,-" should read --4a,10,---

Signed and Sealed this

Fourth Day of July 1978

[SEAL]

Attest:

RUTH C. MASON
Attesting Officer

DONALD W. BANNER
Commissioner of Patents and Trademarks